United States Patent
Joly et al.

(10) Patent No.: US 6,271,429 B1
(45) Date of Patent: *Aug. 7, 2001

(54) PROCESS FOR ISOMERIZING AND DEHYDROGENATING AROMATIC COMPOUNDS CONTAINING EIGHT CARBON ATOMS WITH DIFFERENT CATALYSTS

(75) Inventors: Jean-François Joly, Lyons; Julia Magne-Drisch, Vilette de Vienne; Vincent Coupard, Lyons; Fabio Alario, Neuilly sur Seine; Gérard Miquel, Saint Genis Laval; Marc Reymond, Meyzieux, all of (FR)

(73) Assignee: Institut Francais du Petrole (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/172,290

(22) Filed: Oct. 14, 1998

(30) Foreign Application Priority Data

Oct. 14, 1997 (FR) .................................................. 97 13009

(51) Int. Cl.$^7$ ................................. C07C 5/22; C07C 5/32; C07C 5/367
(52) U.S. Cl. ............................ 585/319; 585/315; 585/481; 585/482; 585/478; 585/477
(58) Field of Search .................................. 585/319, 481, 585/472, 478, 477, 315

(56) References Cited

U.S. PATENT DOCUMENTS

| | | | |
|---|---|---|---|
| 3,409,686 | * 11/1968 | Mitsche | 260/668 |
| 3,553,276 | * 1/1971 | Berger et al. | 260/668 |
| 3,998,900 | * 12/1976 | Wilhelm | 260/668 D |
| 4,062,903 | * 12/1977 | Jacobson | 260/668 A |
| 4,255,606 | 3/1981 | Tse | 585/482 |
| 6,057,486 | 5/2000 | Merlen et al. | 585/481 |

FOREIGN PATENT DOCUMENTS

| | | |
|---|---|---|
| 0 369 078 | 5/1990 | (EP) . |
| 50-16780 | * 6/1975 | (JP) . |

* cited by examiner

Primary Examiner—Walter D. Griffin
Assistant Examiner—Thuan D. Dang
(74) Attorney, Agent, or Firm—Millen, White, Zelano & Branigan, P.C.

(57) ABSTRACT

A process for isomerising a feed comprising aromatic compounds containing 8 carbon atoms is carried out in two steps: an isomerisation step and a dehydrogenation step. In FIG. 1, the feed to be treated is introduced into isomerisation zone R1 via line 1. Substantially pure hydrogen is introduced into line 1 via line 12 and recycled hydrogen is introduced into line 1 via line 13. Hydrogen which circulates in line 13 is purged via line 15. The effluent from isomerisation zone R1 is sent to a separation zone S1 via line 2. In S1, hydrogen contained in the effluent is isolated and recycled to the inlet to isomerisation zone R1 via line 13, the remaining effluent being evacuated from this separation zone S1 via line 3. The fluid contained in line 3 is heated in an oven F1 then evacuated therefrom via line 4. The effluent leaving the oven is enriched in recycled hydrogen via line 14 then it is introduced into dehydrogenation zone R2. The effluent from zone R2 is sent via line 5 to separation zone S2. In S2, hydrogen contained in the effluent is isolated and recycled to the inlet to dehydrogenation zone R2 via line 14, the remainder of the effluent being evacuated from separation zone S2 via line 6. Hydrogen which circulates in line 14 is purged via line 16.

21 Claims, 2 Drawing Sheets

Figure 1:
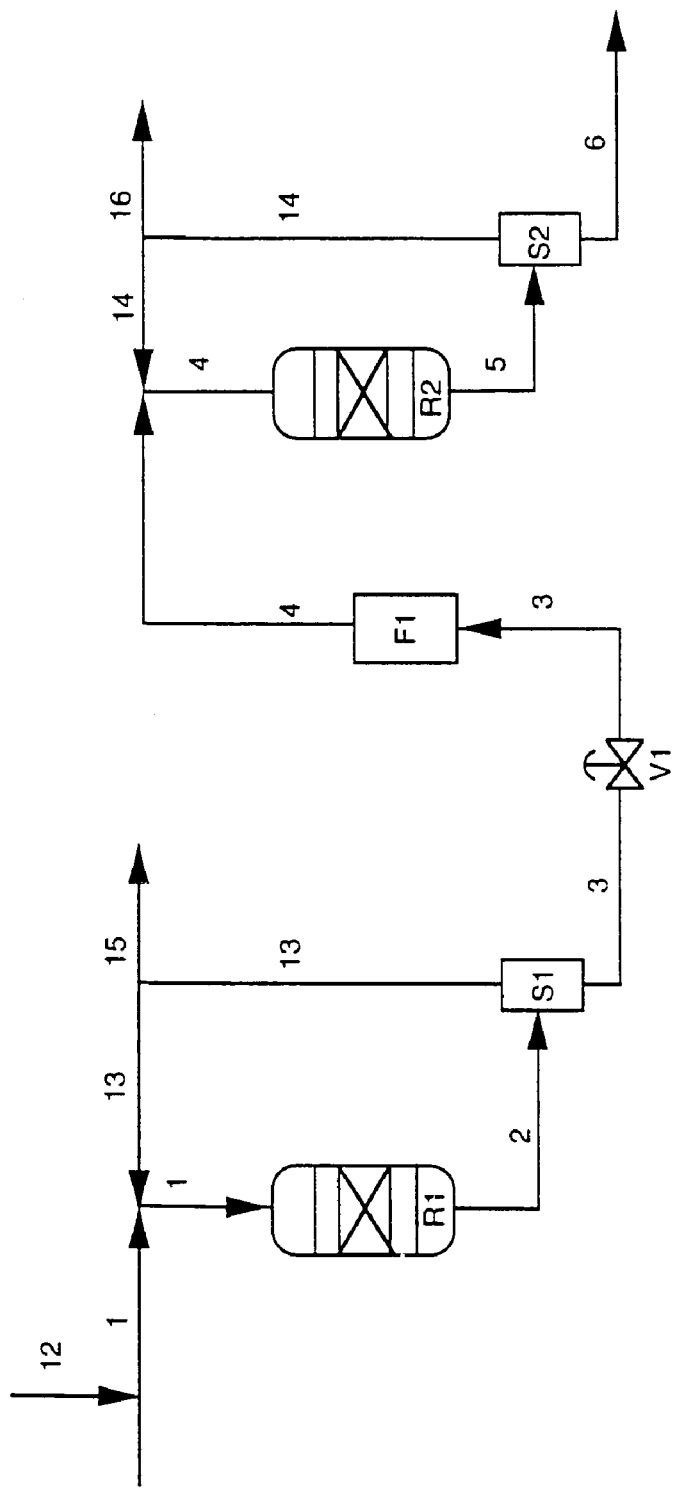

PROCESS FOR ISOMERIZING AND DEHYDROGENATING AROMATIC COMPOUNDS CONTAINING EIGHT CARBON ATOMS WITH DIFFERENT CATALYSTS

FIELD OF THE INVENTION

The present invention relates to the field of isomerising aromatic compounds containing eight carbon atoms.

BACKGROUND OF THE INVENTION

In known processes for isomerising aromatic compounds containing eight carbon atoms, a feed, which is generally depleted in para-xylene with respect to the thermodynamic equilibrium of the mixture (i.e., where the para-xylene content is substantially lower than that of a mixture at thermodynamic equilibrium at the temperature under consideration, that mixture being constituted by meta-xylene, ortho-xylene, para-xylene and ethylbenzene) and generally rich in ethylbenzene with respect to that same mixture at thermodynamic equilibrium, is introduced into a reactor containing at least one catalyst, under suitable temperature and pressure conditions to obtain at the outlet from that reactor a composition of aromatic compounds containing eight carbon atoms which is as close as possible to the composition of that mixture at thermodynamic equilibrium at the reactor temperature.

From that mixture, the para-xylene and possibly ortho-xylene are separated out since they are the isomers which are sought as they are of importance, in particular to the synthetic fibre industry. The meta-xylene and ethylbenzene can then be recycled to the isomerisation reactor inlet so as to increase the production of para-xylene and ortho-xylene. When ortho-xylene is not to be recovered, it is recycled with the meta-xylene and the ethylbenzene.

Reactions for isomerising aromatic compounds containing eight carbon atoms per molecule, however, encounter a number of problems caused by secondary reactions. Thus in addition to the principal isomerisation reaction, hydrogenation reactions are observed such as hydrogenation of aromatic compounds to naphthenes, also naphthene ring opening reactions which lead to the formation of paraffins containing at most the same number of carbon atoms per molecule as the naphthenes from which they originate. Cracking reactions are also observed, such as paraffin cracking which leads to the formation of light paraffins typically containing 3 to 5 carbon atoms per molecule, and dismutation and transalkylation reactions which lead to the production of benzene, toluene, aromatic compounds containing 9 carbon atoms per molecule (for example trimethylbenzenes) and heavier aromatic compounds.

The aggregate of such secondary reactions substantially affects the yields of desired products.

The quantity of secondary products formed (primarily naphthenes containing 8 carbon atoms, paraffins containing 8 carbon atoms, benzene, toluene, and aromatic compounds containing 9 or 10 carbon atoms per molecule) depends on the nature of the catalyst and the operating conditions of the isomerisation reactor (temperature, partial pressures of hydrogen and hydrocarbons, feed flow rate).

The skilled person is aware that secondary reactions increase when the para-xylene content in the reactor is close to the amount of para-xylene at thermodynamic equilibrium under the given temperature and pressure conditions.

Optimising the operating conditions and optimising the formulation of the isomerisation catalyst can increase the para-xylene yield, but cannot overcome the losses. Further, research to obtain new catalysts is a long and expensive business.

SUMMARY OF THE INVENTION

We have surprisingly discovered that it is possible to arrive at para-xylene contents close to the para-xylene content at thermodynamic equilibrium while minimising xylene loss by combining at least two reaction steps.

Thus the present invention provides a process for isomerising a feed comprising aromatic compounds containing eight carbon atoms, comprising at least one isomerisation step a) and at least one hydrogenation step b). The invention also provides an apparatus for carrying out the process.

Isomerisation catalysts which can be used in step a) of the process of the invention are: all catalysts which, from a mixture comprising aromatic compounds containing eight carbon atoms, among them xylenes and/or ethylbenzene, can produce a mixture composition—xylenes and ethylbenzene—close to that of the composition of the mixture at thermodynamic equilibrium under the given temperature and pressure conditions, also catalysts which can effect dealkylating isomerisation of ethylbenzene and benzene.

Any catalyst which can dehydrogenate naphthene type compounds to aromatic compounds can be used in step b) of the process of the present invention. At the dehydrogenation reactor outlet, for a given number of carbon atoms per molecule, the aromatic compounds obtained are present in the proportions of thermodynamic equilibrium under the temperature and pressure conditions reigning at the outlet from the reactor.

The catalysts used in the first step of the process of the invention are supported alumina based catalysts which comprise at least one zeolite and at least one noble metal from group VIII of the periodic table (Handbook of Chemistry and Physics, $45^{th}$ edition, 1964–1965); the metal is preferably platinum. The zeolites used are preferably mordenite, omega zeolite, zeolite with structure type MFI or zeolites with an activity as regards dealkylating isomerisation of ethylbenzene to benzene which is approximately of the same type as the activity of MFI zeolite.

Thus in a first step of the process of the present invention, the operating conditions in the isomerisation zone are selected so as to minimise the production of unwanted compounds from reactions which involve acid catalysis reactions (cracking, dealkylation, dismutation, . . . ). These operating conditions are such that production of naphthenes containing eight carbon atoms per molecule is significantly higher—about 10% to 30% by weight of the effluent at the outlet from the isomerisation zone—than the production obtained by conventional processes for isomerising aromatic compounds containing eight carbon atoms—which is generally about 5% to 10% by weight of the effluent at the outlet from the isomerisation zone.

The effluent obtained from the first reaction zone is treated in a second step in a reaction zone containing at least one dehydrogenation catalyst. The operating conditions for this second step may be identical to or different from the operating conditions in the first step; preferably the operating conditions in these two steps are different. The operating conditions in this second step are determined so as to obtain a xylene and ethylbenzene mixture composition which is as close as possible to the composition at thermodynamic equilibrium.

Catalysts for dehydrogenating paraffins and naphthenes are well known to the skilled person. The supports for these catalysts are generally refractory oxides, usually an alumina. These dehydrogenation catalysts comprise at least one noble metal from group VIII of the periodic table and at least one alkali or alkaline-earth element from groups Ia and IIa of the periodic table. The noble group VIII metal is preferably platinum, and the element from groups Ia or IIa of the periodic table is selected from the group formed by magnesium, potassium and calcium.

These dehydrogenation catalysts can also contain thorium and/or at least one element M from groups IVa or IVb of the periodic table. The group IVa or IVb elements are usually selected from the group formed by tin, silicon, titanium and zirconium. Certain dehydrogenation catalysts also contain sulphur and/or a halogen. More particularly, dehydrogenation catalysts described in U.S. Pat. Nos. 3,998,900 and 3,531,543 can be used in the dehydrogenation step of the process of the invention.

Without wishing to be tied to a particular theory, it can be noted that platinum has a hydrogenolysing activity which is expressed to the detriment of the activity for dehydrogenation of paraffins to aromatic compounds. This hydrogenolysing activity can be substantially reduced, and the selectivity of the catalyst as regards the dehydrogenation reaction can be increased, by adding additional element M.

The inorganic refractory supports used often have an acidic nature and can generate unwanted secondary reactions such as cracking or isomerisation reactions. For this reason, the oxide support is generally neutralised by adding at least one alkaline or alkaline-earth element.

In a preferred implementation of the present invention, compounds with a boiling point of about 80° C. to 135° C., preferably selected from the group formed by at least one paraffin containing eight carbon atoms per molecule and/or at least benzene and/or at least toluene and/or at least a naphthene containing eight carbon atoms are added to the feed for the isomerisation zone.

This compound or these compounds are added to the feed to be treated in the form of a recycle and/or in the form of fresh compounds, in quantities such that the percentages by weight of the added compounds with respect to the total feed which enters the reactor are as follows:

the percentage of paraffins containing eight carbon atoms is about 0.1% to 10% by weight, preferably about 0.2% to 2% by weight;

the percentage of naphthenes containing eight carbon atoms is about 0.5% to 15% by weight, preferably about 2% to 8% by weight;

the percentage of toluene is about 0.1% to 10% by weight, preferably about 0.2% to 5% by weight;

the percentage of benzene is about 01% to 10% by weight, preferably about 0.2% to 2% by weight.

The total percentage of added compounds represents about 0.8% to 20% by weight, normally about 2% to 15% by weight, with respect to the total feed entering the isomerisation zone.

In the process of the present invention, the isomerisation step is carried out in the presence of hydrogen which can be introduced in the form of fresh hydrogen, in the form of hydrogen recycled from the outlet from the isomerisation zone, or in the form of hydrogen recycled from the outlet from the dehydrogenation zone. The operating conditions for the isomerisation step are as follows: a reaction temperature at about 300° C. to 500° C., preferably about 320° C. to 380° C., a partial pressure of hydrogen of about 3 to 15 bars absolute, preferably about 7 to 12 bars absolute, a total pressure of about 4 to 20 bars absolute, preferably about 6 to 15 bars absolute, and an HSV (weight of feed/weight of catalyst/hour) of about 0.2 to 10 $h^{-1}$, preferably about 3 to 6 $h^{-1}$.

In the process of the present invention, the dehydrogenation step is carried out in the presence of hydrogen which can be introduced in the form of fresh hydrogen, in the form of hydrogen recycled from the outlet from the isomerisation zone or in the form of hydrogen recycled from the outlet from the isomerisation zone or in the form of hydrogen recycled from the outlet from the dehydrogenation zone.

The operating conditions for the dehydrogenation step are: a temperature of about 300° C. to 500° C., preferably about 400° C. to 420° C., an absolute partial pressure of hydrogen of about 1 to 15 bars, preferably about 4 to 10 bars, a total absolute pressure of about 2 to 20 bars, preferably about 5 to 15 bars, and an HSV (weight of feed/weight of catalyst/hour) of about 0.2 to 10 $h^{-1}$, preferably about 3 to 6 $h^{-1}$.

The present invention also provides an apparatus for carrying out the process of the invention, comprising at least one conduit for adding a feed to an isomerisation zone, at least one conduit for adding hydrogen to an isomerisation zone, at least one isomerisation zone, at least one conduit via which the effluent from said isomerisation zone is introduced into a zone for separating hydrogen, at least one zone for separating hydrogen, at least one conduit via which hydrogen is evacuated, at least one conduit via which the effluent from said zone for separating hydrogen containing no hydrogen is introduced into an oven, at least one oven, at least one conduit via which the effluent from said oven is sent to a dehydrogenation zone, at least one conduit for adding hydrogen to the dehydrogenation zone, at least one dehydrogenation zone, at least one conduit via which the effluent from said dehydrogenation zone is sent to a second zone for separating hydrogen, at least one second hydrogen separation zone, at least one conduit via which hydrogen is evacuated, and at least one conduit for evacuating effluent containing no hydrogen.

Further, aromatic compounds containing eight carbon atoms contained in the effluent from the dehydrogenation zone can also be recycled after having extracted the desired compounds, i.e., para-xylene and possibly ortho-xylene.

In a variation, the apparatus of the present invention further comprises at least one zone for separating aromatic compounds containing eight carbon atoms, at least one conduit for evacuating aromatic compounds containing eight carbon atoms, at least one conduit for evacuating compounds other than aromatic compounds containing eight carbon atoms, at least one zone for separating compounds with a boiling point of about 80° C. to 135° C., at least one conduit for recycling said compounds to the isomerisation zone, and at least one conduit for evacuating the remainder of the effluent.

FIG. 1 shows a simple implementation of the process of the invention.

In this Figure, the feed to be treated is introduced into isomerisation zone R1 via line 1. Substantially pure hydrogen is introduced into line 1 via line 12 and recycled hydrogen is introduced into line 1 via line 13. Hydrogen which circulates in line 13 is purged via line 15. The effluent from isomerisation zone R1 is sent to a separation zone S1 via line 2. In S1, the hydrogen contained in the effluent is isolated and recycled to the inlet to isomerisation zone R1 via line 13, the remainder of the effluent being evacuated from this separation zone S1 via line 3. This line 3 is provided with a pressure regulation valve V1. The fluid contained in line 3 is heated in an oven F1 then evacuated from the oven via line 4. The effluent leaving the oven is sent into line 4, it is enriched in recycled hydrogen via line 14 then it is introduced into dehydrogenation zone R2. The effluent from zone R2 is sent via line 5 to separation zone S2. In S2, the hydrogen contained in the effluent is isolated and recycled to the inlet to dehydrogenation zone R2 via line 14, the remainder of the invention is evacuated from separation zone S2 via a line 6. Hydrogen which circulates in line 14 is purged via line 16.

Figure 2:
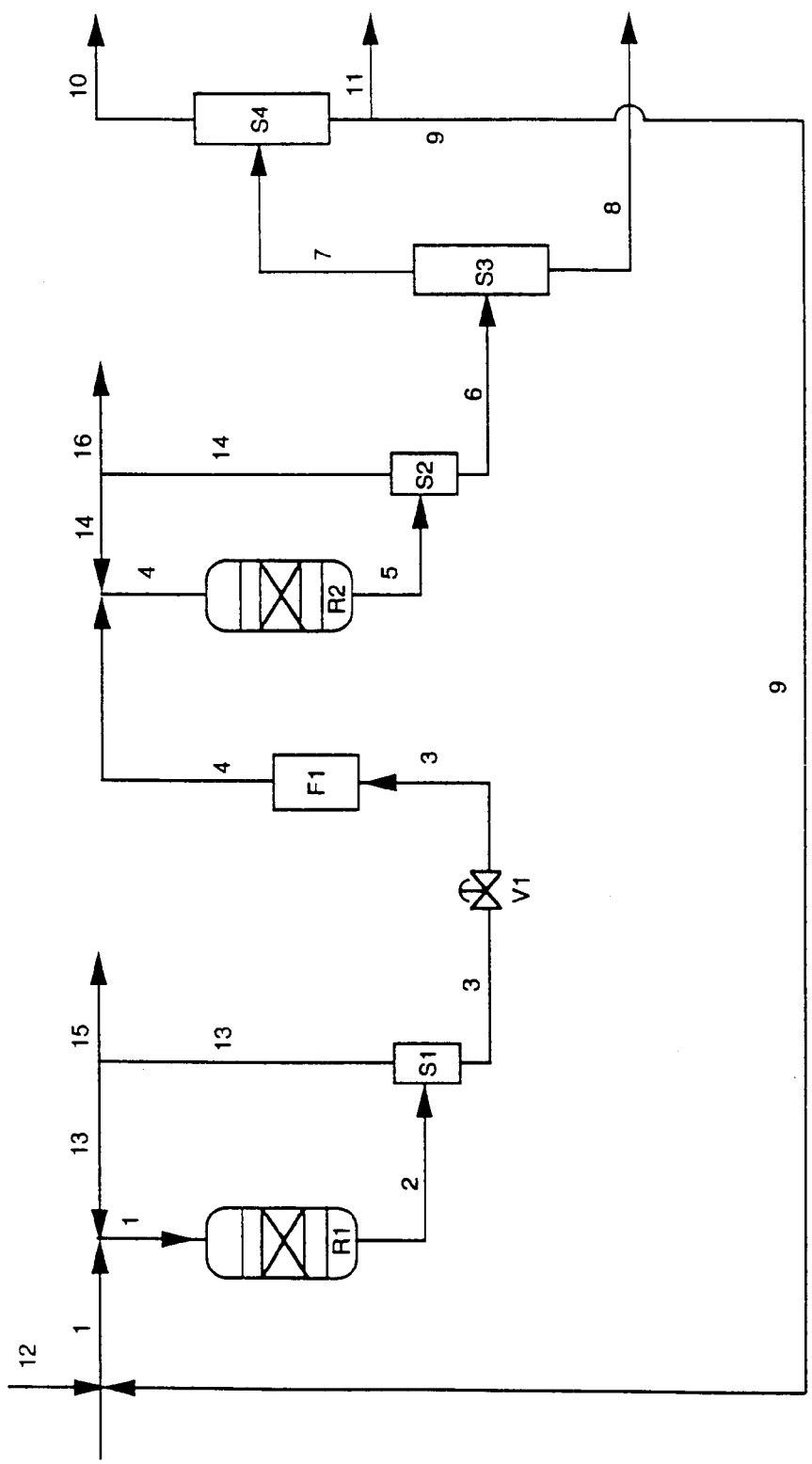

FIG. 2 shows a preferred implementation of the process of the invention.

In this figure, the feed to be treated is introduced into the isomerisation zone R1 via line 1. Before being injected into isomerisation zone R1, this fresh feed is enriched via line 9 with a recycled mixture comprising paraffins containing eight carbon atoms, benzene, toluene and naphthenes containing eight carbon atoms. Substantially pure hydrogen is introduced into line 1 via line 12 and recycled hydrogen is introduced into line 1 via line 13. Hydrogen which circulates in line 13 is purged via line 15.

The effluent from isomerisation zone R1 is sent to a separation zone S1 via line 2. In S1, the hydrogen contained in the effluent is isolated and recycled to the inlet to isomerisation zone R1 via line 13, the remainder of the effluent being evacuated from this separation zone S1 via line 3. This line 3 is provided with a pressure regulation valve V1. The fluid contained in line 3 is heated in an oven F1 then evacuated from the oven via line 4. The effluent leaving the oven is sent into line 4, it is enriched in hydrogen recycled via line 14 then it is introduced into dehydrogenation zone R2. The effluent from zone R2 is sent via line 5 to separation zone S2. In S2, the hydrogen contained in the effluent is isolated and recycled to the inlet to dehydrogenation zone R2 via line 14, the remainder of the effluent being evacuated from separation zone S2 and introduced into separation zone S3 via a line 6. A purge of hydrogen which circulates in line 14 is carried out via line 16. In separation zone S3, the reaction products are separated into two fractions: a light fraction which contains paraffins, naphthenes and the lightest aromatic compounds: benzene and toluene are sent via line 7 into a separation zone S4; the other fraction comprises the aromatic compounds containing at least eight carbon atoms and is evacuated from the apparatus via line 8.

In separation zone S4, compounds with a boiling point of about 80° C. to 135° C. are separated from other hydrocarbons containing one to seven carbon atoms. Compounds with a boiling point of about 80° C. to 135° C. are evacuated from S4 via line 9, a portion of these compounds is purged via line 11; the other portion of these compounds with a boiling point of about 80° C. to 135° C. circulating in line 9 feeds into line 1. Hydrocarbons containing one to seven carbon atoms are evacuated from the apparatus via line 10.

The following examples illustrate the invention without limiting its scope.

EXAMPLES

The isomerisation catalyst for a cut containing aromatic compounds containing eight carbon atoms used in the following examples comprised a mordenite type zeolite and 0.3% by weight of platinum.

The starting zeolite was a mordenite in its sodium form, with an Si/Al ratio of 5.2 and with a unit cell volume of 2.794 nm$^3$ (manometers, i.e., 10$^{-9}$ m). The zeolite underwent three ion exchange steps carried out with a 10 N NH$_4$NO$_3$ solution (10 N indicates that the solution was 10 times normal) at about 100° C. for 4 hours. The solid obtained contained 25 ppm of sodium.

This zeolite in its hydrogen form was then formed by extrusion with an alumina gel to obtain, after drying and calcining in dry air, a catalyst which contained 15% by weight of mordenite zeolite in its hydrogen form and 85% by weight of alumina.

This catalyst underwent anion exchange with hexachloroplatinic acid in the presence of a competing agent (hydrochloric acid), to deposit 0.3% by weight of platinum with respect to the total weight of the catalyst. The wet solid was dried at 120° C. for 12 hours and calcined in a flow of dry air at a temperature of 500° C. for 1 hour. The catalyst obtained contained 14.96% by weight of mordenite in its hydrogen form, 84.76% by weight of alumina and 0.28% by weight of platinum.

The dehydrogenation catalyst used was an alumina based catalyst containing 0.6% by weight of platinum, 0.9% by weight of tin, 0.9% by weight of potassium and 0.6% by weight of chorine.

Example 1

In Accordance with the Invention

A pilot unit as shown in FIG. 1 of the present text, characterized by the presence of two reactors in series, each being equipped with a hydrogen recycle and with a pressure regulation valve located between the two reactors, was used. Each of the reactors was electrically heated and thus operated in isothermal mode.

Each reactor contained 60 g of catalyst.

The feed to be converted was a mixture of aromatic compounds containing eight carbon atoms with a composition as shown in Table 1 below.

The feed flow rate was 180 g/h.

The operating conditions were as follows.

In the isomerisation reactor (R1), the temperature was 370° C., the partial hydrogen pressure was 8.3 bars absolute and the total pressure was 11 bars absolute.

In the dehydrogenation reactor (R2), the temperature was 400° C., the hydrogen partial pressure was 6 bars absolute and the total pressure was 9 bars absolute.

The compositions by weight of the feed and the effluents at the outlet from the 2 reactors is shown in Table 1 below.

The following abbreviations are used in the following examples: "$C_1$–$C_6$ paraffins" means paraffins containing 1 to 6 carbon atoms; "$C_5$ to $C_9$ naphthenes" means naphthenes containing 5 to 9 carbon atoms; and "$C_9^+$ aromatics" means aromatic compounds containing 9 carbon atoms or more.

TABLE 1

| Compounds | Inlet | R1 outlet | R2 outlet |
|---|---|---|---|
| $C_1$-$C_6$ paraffins | 0 | 0.53 | 0.61 |
| $C_5$ to $C_9$ naphthenes | 0 | 21.36 | 2.52 |
| Benzene | 0 | 0.12 | 0.15 |
| Toluene | 0 | 0.49 | 0.70 |
| Ethylbenzene | 14.39 | 7.06 | 8.44 |
| Para-xylene | 1.54 | 15.35 | 19.26 |
| Meta-xylene | 58.07 | 36.93 | 45.69 |
| Ortho-xylene | 26.00 | 16.74 | 20.75 |
| $C_9^+$ aromatic compounds | 0 | 1.42 | 1.88 |

Example 2

Comparative

In Example 2, a single reactor was used with the same isomerisation catalyst as that described for Example 1. The feed to be treated was identical to that of Example 1. The feed flow rate was identical to that of Example 1. The operating conditions were those given for the dehydrogenation reaction in Example 1: the temperature was 400° C., the hydrogen partial pressure was 6 bars absolute and the total pressure was 9 bars absolute. On fixing the operating conditions, a content of naphthenes containing 5 to 9 carbon atoms at the reactor outlet was caused to be close to that obtained at the outlet from the dehydrogenation reactor of Example 1.

The compositions by weight of the feed and effluent leaving the reactor are shown in Table 2 below:

TABLE 2

| Compounds | Inlet | R outlet |
|---|---|---|
| $C_1$-$C_6$ paraffins | 0 | 1.24 |
| $C_5$ to $C_9$ naphthenes | 0 | 2.43 |
| Benzene | 0 | 0.92 |
| Toluene | 0 | 3.09 |
| Ethylbenzene | 14.39 | 9.65 |
| Para-xylene | 1.54 | 18.57 |
| Meta-xylene | 58.07 | 41.24 |
| Ortho-xylene | 26.00 | 18.46 |
| $C_9^+$ aromatic compounds | 0 | 4.40 |

The composition by weight of the effluent leaving the second reactor of Example 1 and the composition by weight of the effluent leaving the reactor of Example 2 are shown in Table 3.

TABLE 3

| Compounds | R outlet | R2 outlet |
|---|---|---|
| $C_1$-$C_6$ paraffins | 1.24 | 0.61 |
| $C_5$ to $C_9$ naphthenes | 2.43 | 2.52 |
| Benzene | 0.92 | 0.15 |
| Toluene | 3.09 | 0.70 |
| Ethylbenzene | 9.65 | 8.44 |
| Para-xylene | 18.57 | 19.26 |
| Meta-xylene | 41.24 | 45.69 |
| Ortho-xylene | 18.46 | 20.75 |
| $C_9^+$ aromatic compounds | 4.40 | 1.88 |

Table 3 clearly shows the advantage of using the process of the present invention with two reactors in series containing two different catalysts. In order to compare the efficiency of the 2 processes (the process of the present invention and the conventional process), we elected to apply the operating conditions of the dehydrogenation step of Example 1 to Example 2, and we thus obtained the same quantities of naphthenes containing 5 to 9 carbon atoms ($C_5$ to $C_9$ naphthenes) at the R outlet as at the R2 outlet.

Under these conditions, when the process of the invention was used (Example 1), the quantity of para-xylene produced was 17.72% by weight as against 17.03% by weight when the conventional isomerisation process was used (Example 2), the yield of aromatic compounds containing eight carbon atoms was also higher: 94.14% by weight when using the isomerisation process of the invention as against 87.92% by weight when using the conventional isomerisation process. The losses constituted by paraffins containing 1 to 6 carbon atoms ($C_1$–$C_6$ paraffins), naphthenes containing 5 to 9 carbon atoms ($C_5$ to $C_9$ naphthenes) and aromatic compounds containing 9 carbon atoms or more ($C_9^+$ aromatics) were substantially lower. They were 8.07% by weight when using the conventional isomerisation process while they were only 5.01% by weight when using the isomerisation process of the invention.

What is claimed is:

1. A process for isomerising a feed comprising aromatic compounds containing eight carbon atoms selected from the group consisting of ethyl benzene, meta-xylene, ortho-xylene and mixtures thereof, comprising conducting at least one isomerisation step a) carried out at 320 to 380° C. in the presence of an alumina based supported isomerisation catalyst which comprises at least one zeolite and at least one group VIII noble metal to convert said aromatic compounds to substantial amounts of naphthenes and para-xylene; and conducting at least one downstream dehydrogenation step b) on effluent from step a) in contact with a dehydrogenation catalyst comprising a support containing at least one refractory oxide, at least one group VIII noble metal and at least one element from groups Ia or IIa, said effluent from step a) containing 10 to 30% by weight of naphthenes.

2. An isomerisation process according to claim 1, wherein the feed treated in the isomerisation step contains at least ethylbenzene or at least meta-xylene or at least a mixture of ethylbenzene and meta-xylene.

3. An isomerisation process according to claim 1, wherein the isomerisation reaction of step a) is carried out at an absolute hydrogen partial pressure of about 3 to 15 bars, at an absolute total pressure of about 4 to 20 bars and at an HSV (weight of feed/weight of catalyst/hour) of about 0.2 $h^{-1}$ to 10 $h^{-1}$.

4. A process according to claim 3, wherein said at least one zeolite is selected from the group consisting of mordenite, omega zeolite, zeolite having an MFI structure or and a zeolite having a dealkylating isomerization activity of ethyl benzene to benzene which is approximately the same as the activity of said zeolite having an MFI structure.

5. A process according to claim 3, wherein said zeolite is mordenite.

6. A process according to claim 5, wherein the at lest one group VIII metal of said isomerization catalyst is platinum.

7. An isomerization process according to claim 6, wherein the dehydrogenation reaction of step b) is carried out at a temperature of about 400° C. to 420° C., at an absolute hydrogen partial pressure of about 1 to 15 bars, at an absolute total partial pressure of about 2 to 20 bars and at an HSV (weight of feed/weight of catalyst/hour) of about 0.20 $h^{-1}$ to 10 $h^{-1}$.

8. A process according to claim 7, wherein said catalyst for the dehydrogenation reaction comprises aluminum support containing alumina, and wherein the at least one group VIII noble metal is platinum and the at least one element from groups IA or IIA is potassium, said dehydrogenation catalyst further comprising tin.

9. An isomerisation process according to claim 1, wherein the catalyst used to carry out the dehydrogenation reaction of step b) further comprises at least one element selected from the group consisting of thorium and elements from groups IVa and IVb.

10. An isomerisation process according to claim 1, wherein the dehydrogenation reaction of step b) is carried out at a temperature of about 300° C. to 500° C., at an absolute hydrogen partial pressure of about 1 to 15 bars, at an absolute total partial pressure of about 2 to 20 bars and at an HSV (weight of feed/weight of catalyst/hour) of about 0.20 $h^{-1}$ to 10 $h^{-1}$.

11. A process according to claim 10, wherein step b) is carried out at a temperature of about 400° C. to 420° C.

12. An isomerisation process according claim 1, wherein compounds with a boiling point of about 80° C. to 135° C. are added to the fresh feed in the form of a recycle or in the form of fresh compounds or in the form of a recycle and fresh compounds.

13. An isomerisation process according to claim 12, wherein the added compounds represent about 0.8% to 20% of the total feed which enters the reactor.

14. A process according to claim 1, comprising passing the feed and hydrogen to said isomerization zone, withdrawing effluent from said isomerization zone, passing said effluent into a zone for separating hydrogen, evacuating hydrogen from said separating zone, removing effluent depleted of hydrogen from said separating zone, heating said hydrogen-depleted effluent, passing resultant heated effluent to said dehydrogenation zone, removing dehydrogenated effluent from said dehydrogenation zone, passing the dehydrogenated effluent to a zone for separating hydrogen, and removing hydrogen-depleted dehydrogenated effluent from said separating zone.

15. A process according to claim 14, said hydrogen-depleted dehydrogenated effluent comprising a mixture of hydrocarbons, said process further comprising separating aromatic compounds containing at least 8 carbon atoms from said mixture of hydrocarbons, separating hydrocarbon containing less than 8 carbon atoms from said mixture of hydrocarbons, and separating from said hydrocarbons having less than 8 carbon atoms, a fraction having a boiling point of about 80° C. to 135° C., and recycling said fraction to the isomerization zone.

16. A process according to claim 1, wherein the isomerization catalyst contains 14.96% by weight mordenite in its hydrogen form, 84.76% by weight of alumina and 0.28% by weight of platinum, and the dehydrogenation catalyst contains 0.6% by weight of platinum, 0.9% by weight of tin, 0.9% by weight of potassium and 0.6% by weight of chlorine.

17. A process according to claim 1, wherein said dehydrogenation step (b) is conducted at 400 to 420° C.

18. A process according to claim 1, wherein the effluent from step (a) contains greater amounts of naphthenes than para-xylenes.

19. A process according to claim 1, wherein said at least one zeolite is selected from the group consisting of mordenite, omega zeolite, zeolite having an MFI structure and a zeolite having a dealkylating isomerization activity of ethyl benzene to benzene which is approximately the same as the activity of sand zeolite having an MFI structure.

20. A process according to claim 1, wherein said zeolite is mordenite.

21. A process according to claim 20, wherein the at least one group VIII metal of said isomerization catalyst is platinum.

* * * * *